(12) United States Patent
Shea et al.

(10) Patent No.: US 9,056,010 B2
(45) Date of Patent: Jun. 16, 2015

(54) CUP SHEATH TO PREVENT SOFT TISSUE IMPINGEMENT

(75) Inventors: Jeffrey J. Shea, Memphis, TN (US); Russell Nmi Walter, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 97 days.

(21) Appl. No.: 12/993,445

(22) PCT Filed: May 27, 2009

(86) PCT No.: PCT/US2009/045314
§ 371 (c)(1),
(2), (4) Date: Feb. 17, 2011

(87) PCT Pub. No.: WO2009/154989
PCT Pub. Date: Dec. 23, 2009

(65) Prior Publication Data
US 2011/0218639 A1 Sep. 8, 2011

Related U.S. Application Data

(60) Provisional application No. 61/056,321, filed on May 27, 2008.

(51) Int. Cl.
*A61F 2/32* (2006.01)
*A61F 2/30* (2006.01)
*A61F 2/46* (2006.01)
*A61F 2/00* (2006.01)

(52) U.S. Cl.
CPC ........... *A61F 2/30721* (2013.01); *A61F 2/0095* (2013.01); *A61F 2/30728* (2013.01); *A61F 2/4609* (2013.01); *A61F 2002/30718* (2013.01)

(58) Field of Classification Search
CPC ............... A61F 2002/3429; A61F 2002/3438; A61F 2002/3443; A61F 2/34; A61F 2/0095; A61F 2002/30561; A61F 2002/30718; A61F 2002/4681
USPC .................. 623/22.21, 22.24, 22.26; 606/91; 128/850, 853, 854
See application file for complete search history.

(56) References Cited

U.S. PATENT DOCUMENTS

2002/0040245 A1* 4/2002 Lester et al. ............... 623/22.23
2002/0082706 A1* 6/2002 Raugel ....................... 623/22.24
(Continued)

FOREIGN PATENT DOCUMENTS

WO WO 2007/016329 A1 2/2007

OTHER PUBLICATIONS

International Search Report; International PCT Application No. PCT/US2009/045314; Jan. 12, 2010; 2 pages.
(Continued)

*Primary Examiner* — Bruce E Snow
*Assistant Examiner* — Brian Dukert
(74) *Attorney, Agent, or Firm* — Krieg DeVault LLP (57) ABSTRACT

An acetabular cup and sheath assembly comprises a sheath and an acetabular cup. The sheath is configured to receive the acetabular cup within the sheath. The sheath and acetabular cup together are configured to pass through a surgical wound toward an implantation site. The sheath further comprises a penetration structure for passing the acetabular cup through the sheath when the acetabular cup is proximately close to an implantation site.

20 Claims, 5 Drawing Sheets

(56) References Cited

U.S. PATENT DOCUMENTS

2003/0191537 A1   10/2003  Wasielewski
2004/0098134 A1    5/2004  Meulink
2004/0186586 A1*  9/2004  Seyer et al. ............... 623/22.12
2008/0234688 A1*  9/2008  Johnson et al. ................ 606/91

OTHER PUBLICATIONS

International Preliminary Report on Patentability and Written Opinion; International PCT Application No. PCT/US2009/045314; Nov. 30, 2010; 5 pages.

* cited by examiner

CUP SHEATH TO PREVENT SOFT TISSUE IMPINGEMENT

CROSS-REFERENCE TO RELATED APPLICATIONS

This application is a United States National Phase filing of International Application No. PCT/US2009/045314 filed on May 27, 2009 which claims the benefit of U.S. Provisional Application No. 61/056,321 filed May 27, 2008, both of which are is herein incorporated by reference.

RELATED FIELD

The present devices relate generally to improving fixation of acetabular cups, and more particularly to preventing bio matter (such as soft tissue and fatty deposits) from contacting an acetabular shell during delivery through a wound until just prior to impaction.

BACKGROUND

In surgery, it is possible to contaminate an acetabular shell with bio matter, soft tissue, and fatty deposits prior to and during impaction. Each time an acetabular cup is inserted into a body cavity, soft tissues and bio matter can build up on portions of the acetabular cup and become stuck. If these materials gather onto or bind to a porous outer coating of the cup, it could adversely affect bone in-growth and initial "bite" and "fixation". If these materials gather on a smooth inner surface of the cup, it could adversely affect subsequent taper-locking between the cup and a liner. Connections between acetabular cups and liners are generally designed with tight tolerances to form a tight fit. Bio-matter can compromise such a tight fit. The devices aim to provide a novel and unique apparatus and method of preserving the porosity of an acetabular cup during insertion into a body cavity.

Figure 1A:
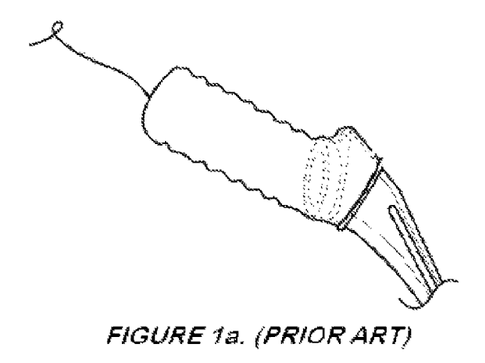
FIGS. 1a-1c illustrate prior art sheaths for use with femoral stems and modular-style necks.
Figure 1B:
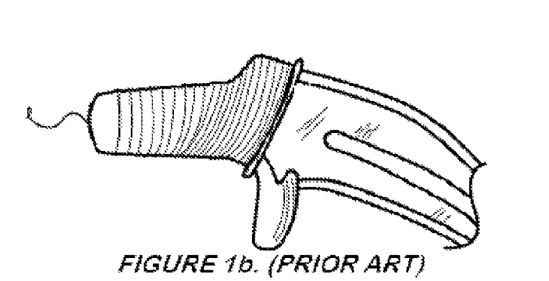
Figure 1C:
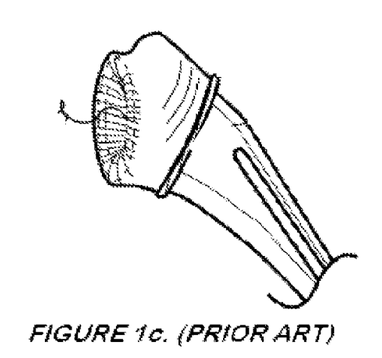

US 2007/100464 AA titled "Orthopaedic implant sleeve and method" and assigned to Zimmer discloses a debris-preventing device for use with modular-style necks and femoral stems. This is shown in FIG. 1. This reference does not disclose use with acetabular cups, and the sheaths shown in this reference teach away from providing a means for acetabular cup penetration as the disclosure is used to protect surfaces proximal to the wound.

Other related art teaches soft tissue protection devices which may be placed over a wound or within a wound. These devices are placed onto or into the wound prior to advancement of a medical device. Such a device only protects the soft tissue covered by the device from damage.

SUMMARY

The aforementioned needs are satisfied by several aspects of the devices.

According to one aspect, there is provided a method of providing a debris-preventing sheath for an acetabular cup. The method includes the steps of: creating a cup-shaped sheath for an acetabular cup which is preferably disposable and somewhat flexible, said sheath having at one end, a means for insertion of the acetabular cup. The means for insertion of the acetabular cup may comprise an open end. At another end opposite said one end, the cup is provided with a means for passage of the acetabular cup. The means for passage may be for instance, a slit, slot, hole, aperture, flap, accordion sleeve, a reduction in diameter, a perforation, a series of perforations, a perforation pattern, a perforation shape, a perforation window, and/or combinations thereof. The means for passage may comprise any shape such as a star, circle, square, pizza slice, etc.

According to another aspect, there is provided a method of using a cup-shaped sheath with an acetabular cup. The method includes the steps of: providing a cup-shaped sheath for an acetabular cup; positioning the cup within the cup-shaped sheath; inserting both of the acetabular cup and cup-shaped sheath into a body cavity; allowing the sheath to shield the acetabular cup from bio-matter (e.g., fatty and soft tissues); allowing the acetabular cup to protrude from or penetrate through said cup-shaped sheath and become affixed to a body portion (e.g., acetabulum); removing the cup-shaped sheath from the acetabular cup and from the body cavity; and, disposing of said cup-shaped sheath. The debris-preventing sheath acts as a shield for a scratchy porous acetabular shell during insertion into a body cavity. Therefore, no biomatter becomes lodged in the porous structure and porosity of the acetabular cup is retained.

Another aspect of the invention provides an acetabular cup and sheath assembly comprising a sheath and an acetabular cup. The sheath is configured to receive the acetabular cup within the sheath. The sheath and acetabular cup together are configured to pass through a surgical wound toward an implantation site. The sheath further comprises a penetration structure for passing the acetabular cup through the sheath when the acetabular cup is proximately close to an implantation site.

According to yet another aspect, there is provided a sterile-packaged implant assembly. The packaged implant assembly comprises: a cup-shaped sheath for an acetabular cup, and an acetabular cup disposed within said cup-shaped sheath; wherein the cup-shaped sheath is provided with a means for passing an acetabular cup through itself; wherein, in use, the cup-shaped sheath allows an acetabular cup to protrude or penetrate through said cup-shaped sheath and become affixed to a body portion; and wherein said cup-shaped sheath prevents build-up and/or generation of debris onto portions of the acetabular cup when the acetabular cup is placed inside a body cavity.

Another aspect of the invention provides a method of implanting an acetabular cup. The method includes forming a sheath for an acetabular cup having at one end, a penetration structure for passage of the acetabular cup through the sheath. A step receives the acetabular cup in the sheath through an end opposite the end having the penetration structure. Another step guides the sheath and the cup through a surgical wound such that the sheath is in front of the cup. Another step removes the sheath from the cup when the cup is proximately near the implantation site.

Further areas of applicability of the present invention will become apparent from the detailed description provided hereinafter. It should be understood that the detailed description and specific examples, while indicating certain embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

The device provides, in part, an improved method of inserting an acetabular cup (i.e., shell) into a body cavity. The method utilizes a sheath that temporarily encloses the acetabular cup during insertion into a body cavity. The sheath protects the cup from bio-matter which could compromise a good taper lock with a liner, or a good initial scratch-fit with bone.

It is preferred that the sheath be sterile-packed with the acetabular cup. The sheath may be incorporated as an integral or separate part of the acetabular cup packaging, or may have a separate part number and used as a disposable instrument. Furthermore, the sheath may be provided as a non-disposable instrument which is configured for multiple sterilizations. The sheath should be somewhat flexible at portions to allow an acetabular cup to penetrate or protrude from one end; however, the sheath may also incorporate more rigid portions at other areas for strength, conformity, and to better push surrounding soft tissues radially-outward away from the acetabular cup. Sheaths may be made so as to be capable of universal use across a variety of differently-sized acetabular cups.

The usefulness of the sheath and methods associated therewith is not limited to acetabular cups. The present device may also be advantageously used with acetabular liners, cages, and/or augments alike such that a surface away from the wound must be passed through the sheath.

FIGS. 1a-1c illustrate sheaths used in the prior art for hip applications. The sheath is disposed on a proximal end of an implant and is used to protect a taper lock. The sheath is not penetrable by the implant, and is meant to roll off the implant. The embodiments of the present invention, however, include a port through which the implant must pass in order to properly position the implant in the bone.

Figure 1D:
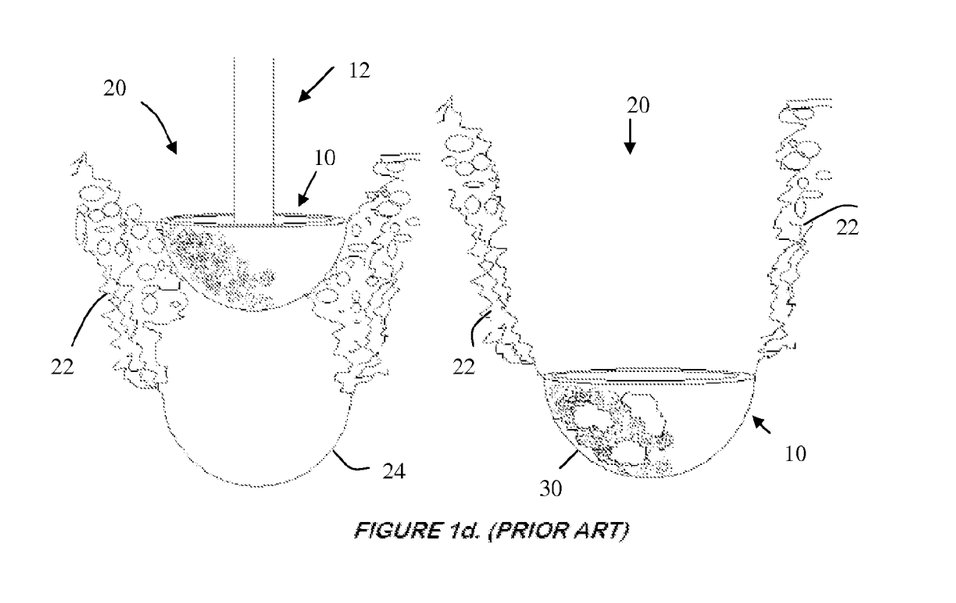
FIG. 1d illustrates the problems associated with the prior art methods.

FIG. 1d illustrates the problems associated with prior art methods. Conventionally, acetabular cups 10 are inserted using a positioner/impactor 12 into a body cavity wound 20 without any protective sheath. The cup 10 is passed through the wound 20 across fatty tissue and soft tissue 22 until the cup 10 is positioned over the prepared acetabulum 24. As the cup 10 is passed, the fatty tissue and soft tissue 22 may brush against the porous surface of the implant. Consequently, fatty tissues and soft tissues 30 cling to the rough, porous, or frictional surfaces of the acetabular cup 10, which are purposely designed for bony ingrowth and initial fixation. With portions or all of the rough, porous, or frictional surfaces "gummed up" by bio-matter, bone ingrowth and the initial fixation "bite" of the acetabular cup 10 is compromised.

Figure 2:
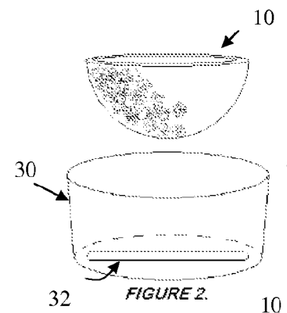
FIG. 2 illustrates one embodiment.

FIG. 2 illustrates one embodiment of a cup-shaped sheath 30 for an acetabular cup 10. The sheath incorporates a means for acetabular cup penetration comprising a single slot 32. The slot 32 is sized such that the cup 10 is retained within the sheath 30 as the shell 10 and sheath 30 are passed through the wound. Once the cup 10 reaches the implant site, then the cup 10 may be pushed through the slot 32 by deformation or tearing of the slot 32 and sheath 30.

Figure 3:
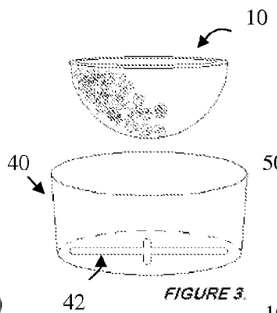
FIG. 3 illustrates another embodiment.

FIG. 3 illustrates another embodiment of a cup-shaped sheath 40 for an acetabular cup 10. The sheath incorporates a means for acetabular cup penetration comprising two generally orthogonal slots 42. While the slots are generally orthogonal, the slots may otherwise by oriented relative to each other such that the give an appropriate amount of clearance to the cup 10 as it passes through the sheath 40. By using multiple slots crossing each other, it may be possible to have thinner or shorter slots than a single slot orientation.

Figure 4:
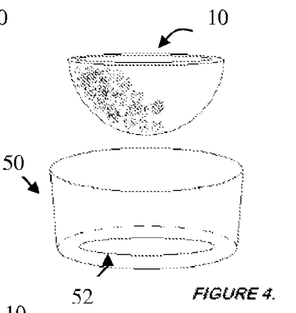
FIG. 4 illustrates yet another embodiment.

FIG. 4 illustrates another embodiment of a cup-shaped sheath 50 for an acetabular cup 10. The sheath incorporates a means for acetabular cup penetration comprising at least one aperture 52. While the aperture 52 is generally oval, other aperture shapes for passing the shell through the sheath may be used such as a round, square or triangular apertures. The size of the aperture should be smaller than the shell but large enough so that the cup may pass through the aperture. Smaller aperture sizes may minimize the contact between the cup and the soft tissue and thus minimize the amount of bio-matter on the porous surface.

Figure 5:
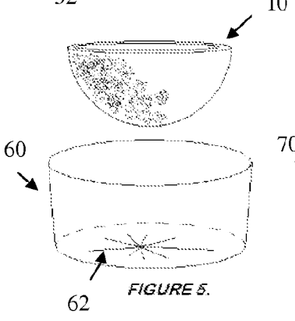
FIG. 5 illustrates yet even another embodiment.

FIG. 5 illustrates another embodiment of a cup-shaped sheath 60 for an acetabular cup 10. The sheath 60 incorporates a means for acetabular cup penetration comprising several circumferentially-spaced, radially-extending slits 62. The slits may be simple cuts through the sheath 60. Such a sheath 60 may preferably be made of a less flexible material so that the triangular wedges made between the slits may retain the shape of the bottom of the sheath 60 and may better retain the cup 10 from passing through the sheath 60 prematurely.

Figures 6, 7:
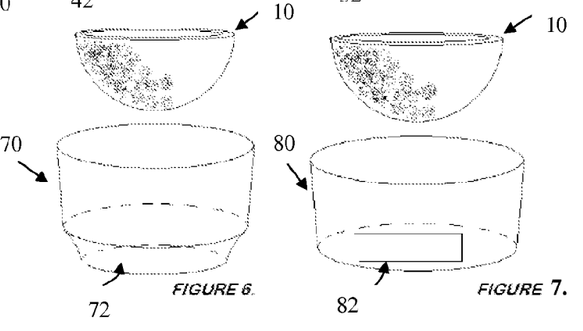
FIG. 6 illustrates another embodiment.
FIG. 7 illustrates yet another embodiment.

FIG. 6 illustrates another embodiment of a cup-shaped sheath 70 for an acetabular cup 10. The sheath 70 incorporates a means for acetabular cup penetration comprising a reduced diameter end 72. The end 72 may be extruded, but again the size of the opening should be less than the size of the cup 10 so that the cup 10 cannot pass through the sheath 70 without some amount of force between the sheath 70 and the cup 10.

FIG. 7 illustrates another embodiment of a cup-shaped sheath 80 for an acetabular cup 10. The sheath 80 incorporates a means for acetabular cup penetration comprising at least one flap 82. The flap may have a reduced width connection portion to facilitate movement and passage of the acetabular cup 10. The flap 82 may be preformed with the sheath using perforations that can be severed after the acetabular cup has passed through the body cavity and is ready for bony contact. The tab 82 may also be cut through the bottom of the sheath 80 and made from a less flexible material such as the sheath 60 of FIG. 5.

Figure 8:
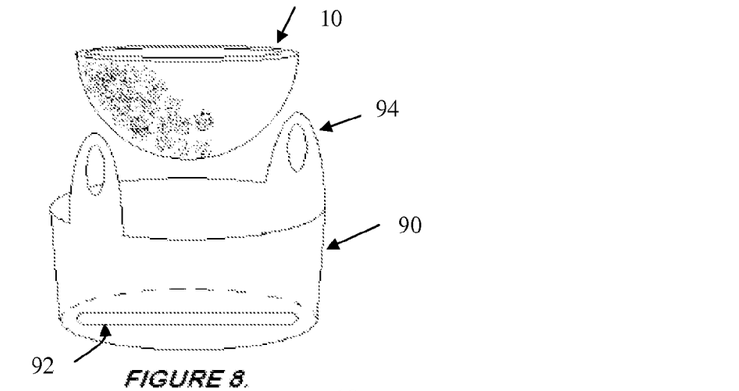
FIG. 8 illustrates yet even another embodiment.

FIG. 8 illustrates another embodiment of a cup-shaped sheath 90 for an acetabular cup 10 having a slot 92 for passing the cup 10. The sheath incorporates at least one removal structure 94 of the sheath 90 from a body cavity. The removal structure 94 may comprise a tab, a hole, an engagement lip, or any other structure which can be engaged to easily remove the sheath 90 from a body cavity. The removal structure 94 may be engaged by the surgeon's fingers, or may be part of a mechanism attached to the impactor which would pull the sheath 90 away from the porous surface of the cup 10.

Figure 9:
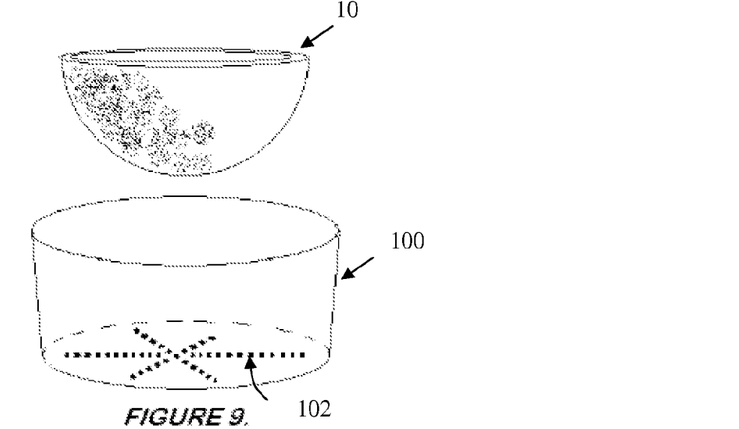
FIG. 9 illustrates another embodiment.

FIG. 9 illustrates another embodiment of a cup-shaped sheath 100 for an acetabular cup 10. The sheath 100 incorporates a means for acetabular cup penetration comprising a perforation pattern 102. The pattern may be in a pizza-slice configuration as shown, in a simple line configuration, or in a flap configuration as shown in FIG. 7. The perforations 102 may allow better isolation of the porous surface from the soft tissue than the embodiments of slots or shapes, but may require more force to push the cup 10 through the sheath 100. Also, complete removal of the sheath 100 (including the tabs at the perforations) may require additional visual acuity during the replacement surgery.

Figure 10:
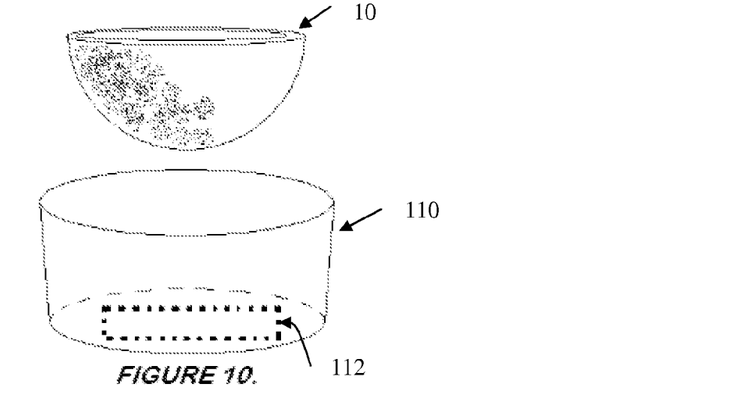
FIG. 10 illustrates yet another embodiment.

FIG. 10 illustrates another embodiment of a cup-shaped sheath 110 for an acetabular cup 10. The sheath 110 incorporates a means for acetabular cup penetration comprising a perforation shape 112. The shape may be in any form and not to be limited to what is shown. For instance, a perforation shape may be comprised of one or more of a triangle, oval, star, polygon, or other multi-sided geometric shape having spline curves.

While the embodiments described above have disclosed many individual forms for the penetration means, it is possible to combine these forms into a single form. For example, a shape similar to the example shown in FIG. 4 may also have a slot or slit extending through remaining portions of the sheath. Such embodiments may allow additional flexibility in the type of material used and the amount of force necessary to push the cup through the sheath.

Figures 11A, 11B, 11C, 12A, 12B, 12C, 12D, 12E:
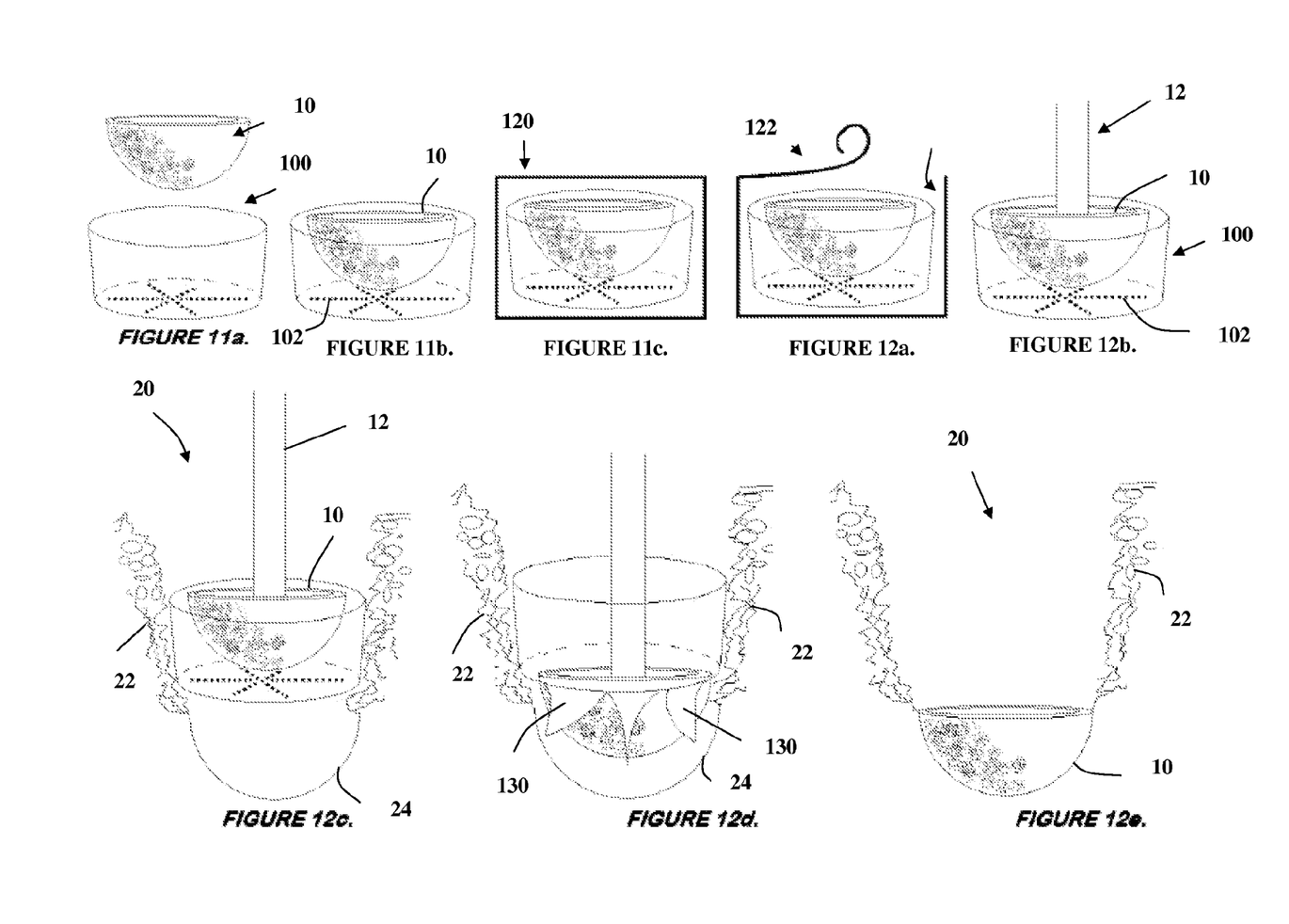
FIGS. 11a-11c illustrate a method of packaging an embodiment.
FIGS. 12a-12e illustrate a method of using an embodiment.

FIGS. 11a-11c illustrate a method of packaging one embodiment. A sheath 100 is packaged with an acetabular cup 10. The assembly is packaged (e.g., using a box or container 120 shown in FIG. 11c) and then sterilized according to conventional methods. The perforation pattern 102 may be any of the penetration means disclosed herein.

FIGS. 12a-12e illustrate a method of using an embodiment. A packaged sheath 100 and acetabular cup 10 assembly is removed from a container 120 (FIG. 12a). An inserter instrument 12 is inserted into the acetabular cup 10 (FIG. 12b). The inserter 12 inserts the acetabular cup 10 through a body cavity 20 (FIGS. 12c-12d) to a prepared acetabulum 24 such that the sheath 100 shields the acetabular cup from contact with "gummy" bio-matter 22 which can clog the outer porous structure of the acetabular cup 10. At the bottom of the body cavity, the acetabular cup 10 protrudes from or penetrates through a means for acetabular cup penetration (FIG. 12d). Flaps 130 on the sheath 100 part to allow the cup to pass through the sheath 100. Finally, the sheath 100 is removed or otherwise generally displaced from the acetabular cup 10, the cup 10 is impacted, and both the sheath 100 and the inserter instrument 12 are removed from the body cavity 20.

In some embodiments, it may be necessary to change the sizes, shapes, lengths, and widths of the slits, slots, flaps, shoulders, etc. to accommodate various shapes and sizes of acetabular cups, shells, augments, cages, etc. and to allow easy penetration of the acetabular cup through the sheath during impaction.

The sheath may be disposable, flexible, colored, non-colored, opaque, transparent, translucent, lubricated, non-lubricated, anatomically-shaped, non-anatomically shaped, cylindrical, implant conforming or cup-shaped, and may have various cross-sectional types. The sheath may be flanged at the open end and configured to rest on bony portions of the acetabular rim, or may be un-flanged to facilitate insertion and withdrawal. The thickness of the sheath may vary. Means provided to the sheath to allow cup penetration can be configured in different ways as would be expected by one having an ordinary skill in the art. Indicia may be provided on the sheath, such as arrows, trademarks, instructions (e.g., for insertion, disposal, orientation, patient or physician info, model number, product number, identification, etc.), or other forms of indicia. Indicia may be moulded in or provided through the usage of inks or dyes. Sheaths may be incorporated with other instruments as an integral unit, or sheaths may be provided with means for effectively facilitating removal from a body cavity—such means may amount to apertures, locking mechanisms, tangs, shelves or ledges for engagement by a tool, etc. In some instances, it may be desirable to incorporate the sheath with a liner inserter guide as one integral unit such as the inserter guide disclosed in co-pending application "Acetabular Liner Inserter Guide" PCT US2008/055323.

While the sheath has been described as having a formed bottom portion, the top portion may also be similarly formed as opposed to open. This may help to further protect the cup from bio-matter and may further allow the surgeon to reposition the sheath and cup by moving the sheath and cup out of the wound. In packaging the cup, the cup would then pass through one side of the sheath in order to get the cup within the sheath and then be passed through the other side during implantation.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The embodiments may improve initial bony fixation by preventing clogging of porous or frictional surfaces on an acetabular cup during insertion into a body cavity. The embodiments may further reduce the risk of liner mal-alignment by keeping most of the inside of the acetabular cup free from debris and soft tissue. The embodiments may even further decrease the risk of an acetabular liner dislodging from its acetabular shell by ensuring that all mating portions between a liner and shell are free from bio-matter.

What is claimed is:

1. An acetabular cup and sheath assembly, comprising:
   a cup-shaped sheath including an interior and a bottom portion; and
   an acetabular cup including an outer bone fixation surface;
   an impactor instrument removably attached to the acetabular cup;
   wherein the acetabular cup is positioned within the interior of the cup-shaped sheath with the bottom portion of the sheath positioned in front of the outer bone fixation surface of the acetabular cup and the impactor instrument extending through an opening in the sheath, the sheath and acetabular cup together configured to pass through a surgical wound toward an implantation site, and wherein the acetabular cup is entirely enclosed within the interior of the cup-shaped sheath;
   wherein the outer bone fixation surface of the acetabular cup comprises an outer hemi-spherical porous frictional surface that is shielded by the bottom portion of the sheath;
   wherein the outer hemi-spherical porous frictional surface of the acetabular cup is enclosed within the interior of the cup-shaped sheath to thereby shield the outer hemi-spherical porous frictional surface from bio-matter; and wherein the bottom portion of the sheath further comprises a penetration structure for passing the acetabular cup through the bottom portion of the sheath when the acetabular cup is proximately close to an implantation site; and wherein the cup-shaped sheath is attached to the impactor instrument to facilitate removal of the cup-shaped sheath subsequent to implantation of the acetabular cup.

2. The acetabular cup and sheath assembly of claim 1, further comprising a removal structure attached to the sheath and configured to remove the sheath from the acetabular cup.

3. The acetabular cup and sheath assembly of claim 1, wherein the penetration structure comprises a perforated slit.

4. The acetabular cup and sheath assembly of claim 1, wherein the bottom portion of the sheath generally conforms to the outer hemi-spherical porous frictional surface of the cup.

5. The acetabular cup and sheath assembly of claim 1, wherein the penetration structure of the sheath is positioned opposite the opening in the sheath through which the impactor instrument extends.

6. The acetabular cup and sheath assembly of claim 1, wherein the cup-shaped sheath includes a side portion extending from the bottom portion to define the interior of the cup-shaped sheath, and wherein the side portion of the cup-shaped sheath extends entirely along the acetabular cup to entirely enclose the acetabular cup within the interior of the cup-shaped.

7. The acetabular cup and sheath assembly of claim 6, wherein the cup-shaped sheath further comprises a top portion configured similar to the bottom portion, the top portion defining an opening sized to receive the acetabular cup into the interior of the cup-shaped sheath and enclosing the acetabular cup to further shield the acetabular cup from bio-matter.

8. The acetabular cup and sheath assembly of claim 1, wherein the penetration structure comprises at least one slot or slit in the bottom portion of the sheath.

9. The acetabular cup and sheath assembly of claim 1, wherein the penetration structure comprises a perforation in the bottom portion of the sheath.

10. An acetabular cup and sheath assembly, comprising:
a cup-shaped sheath including an interior and a bottom portion; and
an acetabular cup including an outer hemi-spherical porous frictional surface;
an impactor instrument removably attached to the acetabular cup;
wherein the acetabular cup is positioned within the interior of the cup-shaped sheath with the bottom portion of the sheath positioned in front of the outer hemi-spherical porous frictional surface of the acetabular cup and the impactor instrument extending through an opening in the sheath; and
wherein the acetabular cup is entirely enclosed within the interior of the cup-shaped sheath to thereby shield the outer hemi-spherical porous frictional surface from bio-matter; and wherein the bottom portion of the sheath includes a penetration feature structured to allow the acetabular cup to pass through the bottom portion of the sheath; and
wherein the cup-shaped sheath is attached to the impactor instrument to facilitate removal of the cup-shaped sheath subsequent to implantation of the acetabular cup.

11. The acetabular cup and sheath assembly of claim 10, wherein the cup-shaped sheath includes a side portion extending from the bottom portion to define the interior of the cup-shaped sheath, and wherein the side portion of the cup-shaped sheath extends entirely along the acetabular cup to entirely enclose the acetabular cup within the interior of the cup-shaped sheath.

12. The acetabular cup and sheath assembly of claim 1, wherein the bottom portion of the cup-shaped sheath encloses a leading end face of the acetabular cup to thereby shield the outer hemi-spherical porous frictional surface.

13. The acetabular cup and sheath assembly of claim 1, wherein the bottom portion of the cup-shaped sheath is positioned distally beyond a leading end of the acetabular cup to thereby shield the outer hemi-spherical porous frictional surface.

14. The acetabular cup and sheath assembly of claim 10, wherein the bottom portion of the cup-shaped sheath encloses a leading end face of the acetabular cup to thereby shield the outer hemi-spherical porous frictional surface.

15. The acetabular cup and sheath assembly of claim 10, wherein the bottom portion of the cup-shaped sheath is positioned distally beyond a leading end of the acetabular cup to thereby shield the outer hemi-spherical porous frictional surface.

16. The acetabular cup and sheath assembly of claim 1, wherein the penetration structure comprises a plurality of radially extending slits that cross over one another.

17. The acetabular cup and sheath assembly of claim 10, wherein the penetration feature comprises a plurality of radially extending slits that cross over one another.

18. The acetabular cup and sheath assembly of claim 1, wherein the cup-shaped sheath further comprises a top wall defining an opening sized to receive the acetabular cup into the interior of the cup-shaped sheath and entirely enclosing the acetabular cup to further shield the acetabular cup from bio-matter.

19. The acetabular cup and sheath assembly of claim 1, further comprising a container;
wherein the acetabular cup is positioned within the interior of the cup-shaped sheath; and
wherein an assembly of the acetabular cup and the cup-shaped sheath are initially packaged within the sterile container to maintain the assembly in a sterilized condition prior to use.

20. The acetabular cup and sheath assembly of claim 10, further comprising a container;
wherein the acetabular cup is positioned within the interior of the cup-shaped sheath; and
wherein an assembly of the acetabular cup and the cup-shaped sheath are initially packaged within the sterile container to maintain the assembly in a sterilized condition prior to use.

* * * * *